(12) United States Patent
Klopsch et al.

(10) Patent No.: US 11,345,680 B2
(45) Date of Patent: May 31, 2022

(54) METHOD FOR PRODUCING BISPYRROLIDINE COMPOUNDS

(71) Applicant: BASF SE, Ludwigshafen am Rhein (DE)

(72) Inventors: Rainer Klopsch, Ludwigshafen am Rhein (DE); Hannes Ferdinand Zipfel, Ludwigshafen am Rhein (DE); Alvaro Gordillo Bolonio, Ludwigshafen am Rhein (DE)

(73) Assignee: BASF SE, Ludwigshafen am Rhein (DE)

( * ) Notice: Subject to any disclaimer, the term of this patent is extended or adjusted under 35 U.S.C. 154(b) by 0 days.

(21) Appl. No.: 16/766,678

(22) PCT Filed: Nov. 13, 2018

(86) PCT No.: PCT/EP2018/080993
§ 371 (c)(1),
(2) Date: May 23, 2020

(87) PCT Pub. No.: WO2019/101568
PCT Pub. Date: May 31, 2019

(65) Prior Publication Data
US 2020/0392115 A1    Dec. 17, 2020

(30) Foreign Application Priority Data
Nov. 23, 2017 (EP) .................................... 17203292

(51) Int. Cl.
*C07D 403/12* (2006.01)

(52) U.S. Cl.
CPC .................. *C07D 403/12* (2013.01)

(58) Field of Classification Search
CPC .................................................. C07D 403/12
See application file for complete search history.

(56) References Cited

U.S. PATENT DOCUMENTS

| 2,525,884 A | 10/1950 | Forcum |
| 9,351,484 B2 | 5/2016 | Musa et al. |

FOREIGN PATENT DOCUMENTS

| CN | 101200445 A | 6/2008 |
| CN | 101948448 A | 1/2011 |
| DE | 4008120 A1 | 9/1990 |
| DE | 102014215388 A1 | 2/2016 |
| EP | 0693466 A1 | 1/1996 |
| EP | 0930293 A1 | 7/1999 |
| WO | 2012/068001 A1 | 5/2012 |
| WO | 2015/020048 A1 | 2/2015 |
| WO | 2016/020139 A1 | 2/2016 |

OTHER PUBLICATIONS

International Preliminary Reporton Patentability received for PCT Patent Application No. PCT/EP2018/080993, dated Jun. 4, 2020, 11 pages (7 pages of English Translation and 4 pages of Original Document).
International Search Report and Written Opinion received for PCT Patent Application No. PCT/EP2018/080993, dated Jan. 23, 2019, 13 pages (6 pages of English Translation and 7 pages of Original Document).
European Search Report for EP Patent Application No. 17203292.2, dated Mar. 8, 2018, 3 pages.
Fakstorp et al., "Bifunctional Amines and Ammonium Compounds. VI. Further Homologs and Analogs of bis-Choline Ether Salts", Acta Chemica Scandinavica, vol. 11, No. 10, 1957, pp. 1698-1705.
Mitsudome et al., "Mild Hydrogenation of Amides to Amines over a Platinum-Vanadium Bimetallic Catalyst", Angewandte Chemie Int. Ed., vol. 56, No. 32, 2017, pp. 9381-9385.
Reppe et al., "Justus Liebigs Annalen der Chemie", Chem. Europe, 1955, pp. 102-104.
Shimizu et al., "Lewis Acid-Promoted Heterogeneous Platinum Catalysts for Hydrogenation of Amides to Amines", ChemistrySelect, vol. 1, Issue 4, 2016, pp. 736-740.
Shostakovska et al., Seriya Khimicheskaya, 1961, pp. 910-913.

*Primary Examiner* — Brian E McDowell
(74) *Attorney, Agent, or Firm* — Faegre Drinker Biddle & Reath LLP

(57) ABSTRACT

The present application relates to a method for preparing compounds of the formula I in which, in a first step, γ-butyrolactone is reacted with diamines of the formula II to form bisamides of the formula Ill, with the amide function of the bisamides of the formula Ill then undergoing partial or complete catalytic hydrogenation in step II) to form bispyrrolidine compounds of the formula I.

7 Claims, No Drawings

METHOD FOR PRODUCING BISPYRROLIDINE COMPOUNDS

CROSS-REFERENCE TO RELATED APPLICATIONS

This application is a national stage application (under 35 U.S.C. § 371) of PCT/EP2018/080993, filed Nov. 13, 2018, which claims benefit of European Application No. 17203292.2, filed Nov. 23, 2017, both of which are incorporated herein by reference in their entirety.

The present application relates to a method for preparing bispyrrolidine compounds of the formula I in which, in a first step, γ-butyrolactone is reacted with diamines of the formula I to form bisamides of the formula III, with the amide function of the bisamides of the formula III then undergoing partial or complete catalytic hydrogenation in step II) to form bispyrrolidine compounds of the formula I.

There is a great demand for compounds used as catalysts in the production of polyurethane foams and which subsequently give rise to little or no emissions. Emissions may take the form of emissions of the catalyst itself or emissions of degradation products such as amines, DMF, and formaldehyde.

Catalysts that are incorporated into the polyurethane network in the course of the reaction and consequently are not released later as emissions are abundant in industry. However, catalysts that release low emissions in the form of amine, DMF, and formaldehyde emissions that for amines are between ≥0 μg/m$^3$ and ≤40 μg/m$^3$, for DMF are in the range from ≥0 to ≤5 ppm, and for formaldehyde are within or below the limits set by foam manufacturers and the furniture industry in Europe and the USA for aldehyde emissions under the terms of the voluntarily imposed "CertiPUR" program, and for formaldehyde emissions in particular, and which are described in more detail in WO 2016/020139, page 4, line 12 to page 6, line 11, are not widely available, not least when the catalytic activity thereof must at the same time be at least as good as the prior art or even better.

WO 2016/020139 describes the preparation of bispyrrolidine compounds of the formula I that are used as catalysts in the production of polyurethane for flexible and rigid foams. However, the bispyrrolidine compounds are here reacted starting from pyrrolidine and 2-chloroethyl ether or from pyrrolidine and diethylene glycol in the presence of an Ru catalyst. The reaction starting from γ-butyrolactone and the diamines corresponding to the formula II is not disclosed here.

WO 2015/20048 describes polyurethane compositions that also use symmetrical bispyrrolidine ether compounds as catalysts. However, the preparation of the exact bispyrrolidine ether compounds of the formula I is not disclosed here.

U.S. Pat. No. 9,351,484 B2 describes the preparation of symmetrical and unsymmetrical bis(1-alkylpyrrolidin-2-one) ethers. The corresponding N-hydroxyalkylpyrrolidones are here dehydrated in the presence of acidic catalysts and the water formed is removed. In the method of the invention, on the other hand, no catalysts that would subsequently need to be removed in a separate step are added. Moreover, the method of the invention is at least one step shorter and thus more economical than the method described in U.S. Pat. No. 9,351,484 B2.

M.-F. Shostakovska et al. in Seriya Khimicheskaya (1961), 910-13 describes the formation of symmetrical and unsymmetrical bis(1-alkylpyrrolidin-2-one) ether compounds starting from N-hydroxyalkylpyrrolidones in the presence of carboxylic acids and sulfuric acid with subsequent azeotropic distillation.

EP 0693466 B1 describes, inter alia, the preparation of 1,1'-(oxybis(ethane-2,1-diyl))bis(pyrrolidin-2-one), which corresponds to a bisamide of the formula III. This bisamide is, however, prepared by a Williamson ether synthesis from 2-pyrrolidinone, potassium hydroxide, a catalyst and bis(2-chloroethyl) ether. A reaction from γ-butyrolactone and compounds of the formula I to form the corresponding bisamide is not disclosed. The bisamide described in EP 0693466 B1 is used as solvent for the halogenation of aromatic compounds.

EP 0930293 B1 describes the preparation of N-vinylpyrrolidone (NVP) by dehydration of N-(2-hydroxyethyl)pyrrolidone (HEP) using a catalyst, with bisamides of the formula III being additionally formed as by-products. The preparation of bisamides of the formula III by reaction of γ-butyrolactone and compounds of the formula II is not described.

Reppe in Liebigs Annalen der Chemie 1955, pages 102-104 describes the reaction of tetrahydrofuran and 1,4-butanediol with ammonia and primary amines to form various products, including the preparation of dipyrrolidylalkanes. However, the use of γ-butyrolactone and the use of a catalyst for the hydrogenation in the second step is not described.

The formation of bispyrrolidines is described in principle in DE 4008120, CN 101948448, U.S. Pat. No. 2,525,884, and many other documents. However, only good selectivities are achieved here with large amine excesses.

J. Falkstorp in Acta Chemica Scandinavica (1957), 11, 1698-1705 discloses the preparation of 1,1'-(oxybis(ethane-2,1-diyl))dipyrrolidine via a Williamson ether synthesis starting from 2-(pyrrolidin-1-yl)ethan-1-ol in the presence of 1-(2-chloroethyl)pyrrolidine and a catalyst. A hydrogenation process as in step II of the method of the invention is not described.

Ken-ichi Shimizu et al in ChemistrySelect 2016, 4, 736-740 describe the hydrogenation of tertiary amides with Pt catalysts attached to Lewis acid supports. The hydrogenation of pyrrolidin-2-one derivatives is described here too. However, the use of bisamides of the formula III in such a hydrogenation is not described.

Kiyotomi Kaneda et al. in Angewandte Chemie Int. Ed. 2017, 56, 9381-9385 describe the hydrogenation of amides to the corresponding amines under mild conditions in the presence of Pt/V catalysts attached to a hydroxyapatite (HAP) support, such as for example the hydrogenation of N-acetylpyrrolidine to the corresponding N-ethylpyrrolidine. The hydrogenation of the bisamide of the formula III is not, however, described.

None of the methods described in the prior art discloses the possibility of preparing bispyrrolidine compounds of the formula I in only two steps starting from γ-butyrolactone with diamines of the formula I to form bisamides of the formula III and subsequent catalytic hydrogenation to form the bispyrrolidine compounds of the formula I without using an excess of amine.

It is according the object of the present invention to provide a simple method for preparing bispyrrolidine compounds of the formula I starting from inexpensive simple starting materials such as γ-butyrolactone in as few steps as possible and without using an excess of amine.

This object is achieved by a method for preparing bispyrrolidine compounds of the formula I

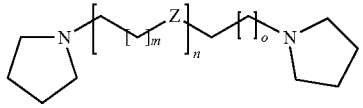

Formula I where
Z is selected from the group consisting of NR, oxygen and carbon, wherein R is selected from the group consisting of hydrogen and linear or branched or cyclic $C_1$-$C_{20}$ substituted or unsubstituted alkyl groups,
n is a whole natural number in the range from 0 to 9,
m and o are independently a natural number in the range from 1 to 12,
wherein in step I) γ-butyrolactone is reacted with diamines of the formula II

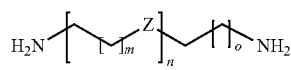

Formula II where Z, n, m, and o are as defined above, to form bisamides of the formula III

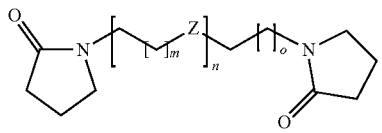

Formula II and then,
in step II), the bisamides of the formula III are catalytically hydrogenated to form the bispyrrolidine compounds of the formula I.

The method of the invention is advantageous when the reaction of γ-butyrolactone with compound II in step I) is carried out at temperatures in the range from 100 to 300° C. with simultaneous or subsequent removal of the excess water by distillation.

The method of the invention is advantageous when step II) is carried out in the presence of a hydrogenation catalyst in which the hydrogenation catalyst comprises at least one metal selected from the group consisting of Cu, Cr, Ni, Co, Fe, Pt, Pd, Re, Ru, and Rh.

The method of the invention is advantageous when step II) is carried out using a heterogeneous catalyst.

The method of the invention is advantageous when step II) is carried out in the presence of a Raney cobalt, Raney nickel or doped or undoped catalyst of the Cu—Cr type.

The method of the invention is advantageous when the hydrogenation in step II) is carried out in the presence of a Raney cobalt catalyst or of a doped catalyst of the Cu—Cr type at temperatures in the range from 100 to 300° C. and at a hydrogen pressure in the range from 100 to 350 bar.

The method of the invention is advantageous when Z is oxygen and n is 1 or 2 and m=o=1.

The method of the invention is advantageous when the compounds of the formula IB, in which —X1 and —X2 are independently selected from the group consisting of hydrogen and double-bond oxygen, but where at least one of —X1 or —X2 is hydrogen, and which may be obtained in step II in addition to the bispyrrolidine compounds of the formula I, may undergo a further catalytic hydrogenation in a further step III).

The method of the invention is advantageous when the hydrogenation in steps II) and III) is carried out using the same catalyst.

The method of the invention is advantageous when the hydrogenation in steps II) and III) can be carried out in a single step.

The method of the invention is advantageous when the compound of the formula I is the bispyrrolidine ether of the formula IA

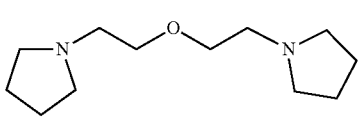

Formula IA

The method of the invention is used to bispyrrolidine compounds of the formula I

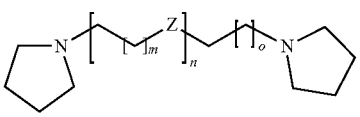

Formula I where Z is selected from the group consisting of O, NR and C. Preference is given to Z=O or NR and very particular preference to Z=O.

R is here selected from the group consisting of hydrogen and linear or branched or cyclic $C_1$-$C_{20}$ substituted or unsubstituted alkyl groups. The linear or branched or cyclic $C_1$-$C_{20}$ alkyl groups are preferably selected from the group consisting of methyl, ethyl, n-propyl, isopropyl, n-butyl, 2-butyl, isobutyl, tert-butyl (2-methylpropan-2-yl), n-pentyl, 2-methylbutyl, 3-methylbutyl, 1,1-dimethylpropyl, 1,2-dimethylpropyl, 2,2-dimethylpropyl, 2-ethylpropyl, n-hexyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 1,1,2-trimethylpropyl, 1,2,2-trimethylpropyl, 1-ethyl-1-methylpropyl, 1-ethyl-2-methylpropyl, 2-ethylbutyl, cyclohexyl, n-heptyl, 2-methylhexyl, 3-methylhexyl, 2,2-dimethylpentyl, 2,3-dimethylpentyl, 3,3-dimethylpentyl, 3-ethylpentyl, 2-ethylhexyl, methylcyclohexyl, n-octyl, 2-methylheptyl, 3-methylheptyl, 4-methylheptyl, 2,2-dimethylhexyl, cis- and/or trans-2,3-dimethylhexyl, 3,3-dimethylhexyl, 2,4-dimethylhexyl, 2,5-dimethylhexyl, cis- or trans-3,4-dimethylhexyl, cis- and/or trans-, 2-methylcyclohexyl, 1,3-dimethylcyclohexyl, 1,4-dimethylcyclohexyl, cis- and/or trans-2,3-dimethylcyclohexyl, cis- and/or trans-3,4-dimethylcyclohexyl, 2,2-dimethylcyclohexyl, 3,3-dimethylcyclohexyl, 4,4-dimethylcyclohexyl, n-nonyl, 2-methyloctyl, 3-methyloctyl, 4-methyloctyl, 2,2-dimethylheptyl, 2,3-dimethylheptyl, 3,3-dimethylheptyl, 2,4-dimethylheptyl, 4,4-dimethylheptyl, 2,2,3-trimethylhexyl, 2,2,4-trimethylhexyl, 2,3,3-trimethylhexyl, 1,2,2-trimethylcyclohexyl, cis- and/or trans-1,2,3-trimethylcyclohexyl, 1,3,3-trimethylcyclohexyl, 2,2,3-trimethylcyclohexyl, cis- or trans-2,3,4- trimethylcyclohexyl, 2,3,3-trimethylcyclohexyl, 2,4,4-trimethylcyclohexyl, 3,4,4-trimethylcyclohexyl, n-decyl, 2-methylnonyl, 3-methylnonyl, 4-methylnonyl, 5-methylnonyl, 2,3-dimethyloctyl, 2,2-dimethyloctyl, 2,4-dimethyloctyl, 3,3-dimethyloctyl, 4,4-dimethyloctyl, 2,3,4-trimethylheptyl, 2,2,3-trimethylheptyl, 2,3,3-trimethylheptyl, 2,4,4-trimethylheptyl, 2,2,4-trimethylheptyl, 2,3,4,5-tetramethylhexyl, 2,2,3,4-tetramethylhexyl, 2,3,3,4-tetramethylhexyl, 2,3,4,4-tetramethylhexyl, cis- and/or trans-1,2,3,4-tetramethylcyclohexyl, 1,2,2,3-tetramethylcyclohexyl, cis- or trans-1,2,3,3-tetramethylcyclohexyl, 1,2,2,4-tetramethylcyclohexyl, undecyl, dodecyl, tridecyl, tetradecyl, pentadecyl, hexadecyl, heptadecyl, octadecyl, nonadecyl, eicosyl, and the constitutional isomers thereof. Particular preference is given to methyl, ethyl, propyl, n-butyl, tert-butyl, n-pentyl, n-hexyl, n-heptyl, n-octyl, n-nonyl, and n-decanyl. Particularly preferred linear or branched or cyclic $C_1$-$C_{20}$ alkyl groups are selected from the group consisting of methyl, ethyl, propyl, n-butyl, tert-butyl, and hexyl. Very particular preference is given to methyl and ethyl. The substituents on the linear or branched or cyclic $C_1$-$C_{20}$ alkyl groups may be any alkyl group already mentioned under the linear or branched or cyclic $C_1$-$C_{20}$ alkyl groups and also those that are additionally substituted or interrupted by heteroatoms. Preferred heteroatoms here are oxygen and nitrogen. Preferred heteroatom-substituted linear or branched or cyclic $C_1$-$C_{20}$ alkyl groups are selected from the group consisting of 2-hydroxyethyl, 3-hydroxypropyl, 4-hydroxybutyl, 2-aminoethyl, 3-aminoethyl, and 4-aminoethyl.

R is preferably selected from the group consisting of hydrogen, 4-buten-1-yl, methyl, ethyl, propyl, n-butyl, hexyl, and 4-hydroxybutyl. R is particularly preferably hydrogen.

n is a whole natural number in the range from 0 to 9, preferably in the range from 1 to 5, more preferably in the range from 1 to 3, most preferably in the range of 1 or 2. The indices m and o may independently be a whole natural number in the range from 1 to 12. In bispyrrolidine compounds of the formula I, m depends on n. When n=1, preferred compounds are those in which m and o are independently a whole number in the range from 1 to 12. Particularly preferred in this instance when n=1 is that m and o are the same number in the range from 1 to 12. When n=2 to 9, preferred compounds are those in which m=1 and o may be a number in the range from 1 to 12. Particularly preferred in this instance when n=2-9 is that m and o=1. Preference is given to bispyrrolidine compounds of the formula I selected from the group in which n, m, and o=1, n=2 where m=1 and o=1, n=3 where m=1 and o=1, and compounds in which n=1 and m and o are identical. Particular preference is given to compounds of the formula I in which n, m and o=1.

Preferred compounds of the formula I are selected from the following group:

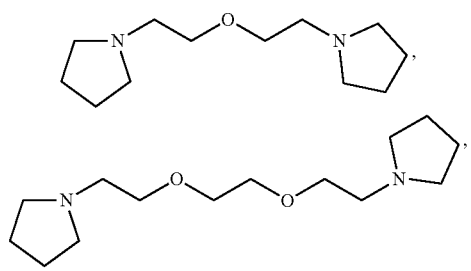

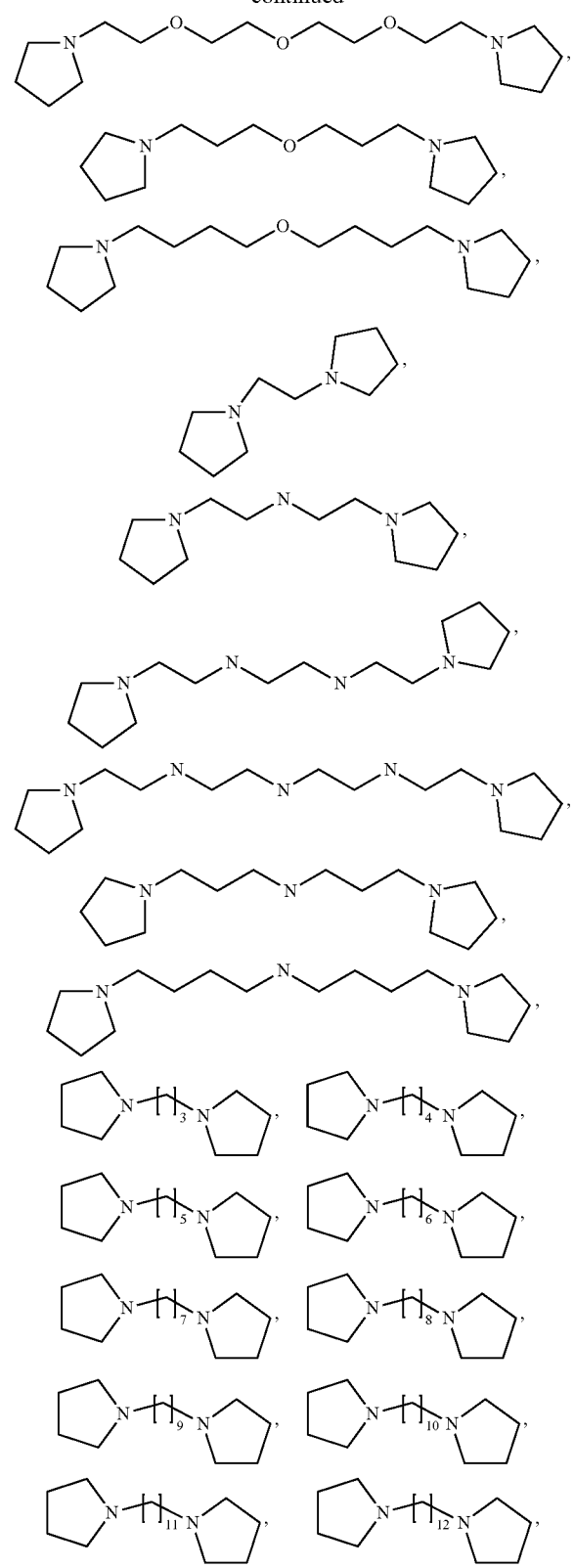

Preferred bispyrrolidine compounds of the formula I are those in which Z=O or NR, n and m=1, and o is a whole number in the range from 1 to 12. Particular preference is given to the bispyrrolidine compound of the formula IA

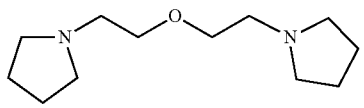

Formula IA

In the method of the invention, in step I γ-butyrolactone is reacted with the diamine of the formula II. In the diamine of the formula II, Z, m, and o have the same meaning as in the bispyrrolidine compounds of the formula I.

The reaction of the diamine of the formula II with γ-butyrolactone may be carried out in the presence of a solvent. Preference is, however, given to carrying out the reaction without solvent.

The reaction of γ-butyrolactone with the diamine of the formula II is carried out at temperatures in the range from 150 to 400° C., preferably in the range from 200-350, more preferably in the range from 250-300° C. The water of reaction that is formed may be removed by distillation at the same time.

In step II of the method of the invention, the bisamide of the formula III obtained from step I is catalytically hydrogenated. The hydrogenation may be preceded by a drying step such as distillation or conventional drying with drying agent, but this is not mandatory. In the bisamides of the formula III, Z, m, and o have the same meaning as in the bispyrrolidine compounds of the formula I.

The catalyst used in step II may be any catalyst that is capable of hydrogenating amide groups to the corresponding secondary amines. The hydrogenation in step II may be catalyzed either homogeneously or heterogeneously. Preference is given to using heterogeneous catalysts. The catalysts for the hydrogenation comprise at least one metal selected from the group consisting of Cu, Cr, Ni, Co, Fe, Pt, Pd, Re, Ru, and Rh. The catalysts may also be doped with further metals selected from the group consisting of alkali metals, alkaline earth metals, and metals from subgroups 3 to 8 of the periodic table. The doping metals are preferably selected from the group consisting of Li, Na, K, Mg, Ca, Ba, W, Mo, V, Mn, P, B, and Sn. The catalysts may be attached to different support materials. The support materials are selected from the group consisting of silicon dioxide, carbon, titanium dioxide, aluminum oxide $Al_2O_3$, niobium oxide $Nb_2O_5$, cerium oxide $CeO_2$, silicon carbide SiC, and zirconium oxide $ZrO_2$. These supports too, like the metals themselves, may be doped with the same doping metals as described above. In addition to the individual doped or undoped active metals on the doped or undoped support materials, bimetallic catalysts can also be used. These are selected from the group consisting of Pt—Nb, Pt—V, Rh—Mo, Ru—Mo, Ru—Re, Rh—Re, Pt—Re, Pd—Re, Rh—W, and Cu—Cr (for example copper chromite catalysts). These bimetallic catalysts may likewise be doped with the above dopants both in the active metal and in the support. Particular preference is given to catalysts selected from the group consisting of Raney Co, Raney Ni, catalysts of the doped or undoped copper chromite type such as Cu—Cr, Cu—Cr/Mn, and Cu—Cr/Ba. Very particular preference as catalysts is given to Raney Co and to doped Cu—Cr/Ba type copper chromite catalysts.

The hydrogenation in step II is carried out in the presence of pure and/or synthetic hydrogen or mixtures of hydrogen with other inert gases selected from the group consisting of nitrogen and argon. The hydrogenation may be in the presence of solvents selected from the group consisting of ammonia, ethers, alcohols, hydrocarbons, alkyl aromatics, and mixtures of such compounds. Preferred ethers are selected from the group consisting of glyme, diglyme, proglyme, THF, and dioxane. Preferred alcohols are selected from the group consisting of methanol, ethanol, n-propanol, isopropanol, n-butanol, sec-butanol, isobutanol, tert-butanol, 1-pentanol, 2-pentanol, 3-pentanol, 1-hexanol, 2-hexanol, 3-hexanol, heptanol, ethylhexanol, and propylheptanol. Preferred hydrocarbons are selected from the group consisting of butane, pentane, hexane, heptane, octane, nonane, decane, undecane, dodecane, and linear and branched isomers and mixtures thereof. Preferred alkyl aromatics are selected from the group consisting of benzene, toluene, and xylene.

Preferred mixtures of solvents are selected from the group consisting of ethers with alcohols, alcohols and hydrocarbons, alcohols and alkyl aromatics, hydrocarbons and alkyl aromatics, wherein the alcohols and hydrocarbons may be aliphatic, cyclic or cycloaliphatic. During the hydrogenation in step II, additional additives may also be present. These are selected from the group consisting of alkylated amines, which may be mono-, di- or trialkylated. Examples of monoamines are methylamine, ethylamine, propylamine, butylamine, pentylamine, hexylamine, heptylamine, octylamine, nonylamine, decylamine, undecylamine, and dodecylamine. Examples of dialkylamines are dimethylamine, diethylamine, dipropylamine, dibutylamine, dipentylamine, dihexylamine, diheptylamine, dioctylamine, dinonylamine, didecylamine, diundecylamine, and didodecylamine. Examples of trialkylamines are trimethylamine, triethylamine, tripropylamine, tributylamine, tripentylamine, trihexylamine, triheptylamine, trioctylamine, trinonylamine, tridecylamine, triundecylamine, and tridodecylamine. Further substituents for amines may be linear or branched or cyclic $C_1$-$C_{20}$ alkyl groups and alkoxides. The linear or branched or cyclic $C_1$-$C_{20}$ alkyl groups are here the same linear or branched or cyclic $C_1$-$C_{20}$ groups that can also serve as R in the formula I. The temperature during the hydrogenation is in the range from 50 to 300° C., preferably in the range from 100 to 250° C., more preferably in the range from 150 to 250° C. The pressure during the hydrogenation is in the range from 100 to 350 bar, preferably in the range from 150 to 300 bar, more preferably in the range from 150 to 250 bar.

The product obtained from step II may then be a mixture of the possible bispyrrolidine compounds of the formula I and compounds of the formula IB.

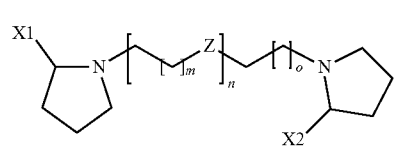

Formula IB in which —X1 and —X2 are independently selected from the group consisting of hydrogen and double-bond oxygen, but where at least one of —X1 or —X2 is hydrogen. However, the product from step II according to the invention may also be completely hydrogenated, with the result that bispyrrolidine compounds of the formula I are already obtainable after step II. In this instance, step III according to the invention is not necessary.

Step III according to the invention is a further hydrogenation of the compounds of the formula IB obtained in step II in which —X1 and —X2 are independently selected from the group consisting of hydrogen and double-bond oxygen, but where at least one of —X1 or —X2 is hydrogen.

This hydrogenation too is carried out in the presence of pure hydrogen or mixtures of hydrogen and other inert gases selected from the group consisting of nitrogen and argon. Temperature and pressure are here the same preferred temperature ranges and pressure ranges as in step II. The set temperatures and pressures in step III do not, however, need to be identical to those in step II.

The hydrogenation catalysts used here can be the same catalysts as are used in step II of the method. For step III of the method, hydrogenation with a heterogeneous catalyst is preferred. Particular preference is given to hydrogenation in the presence of Raney Co or to doped Cu—Cr/Ba type copper chromite. If the catalyst, temperature, and pressure in steps II and III are identical, then it is also possible to combine these two steps in step II.

After step II and/or step III, the resulting mixture comprising the compounds of the formula I may still be worked up by distillation. This can be done using any distillation column known to those skilled in the art. Workup by distillation is preferably carried out under reduced pressure and at elevated temperatures and in one or more columns having a plurality of theoretical plates. This workup by distillation is preferably carried out at a pressure in the range from 10 to 150 mbar, temperatures in the range from 60 to 230° C., and with columns having a number of theoretical plates in the range from 25 to 30.

EXAMPLES

Example 1: Method for Preparing 1,1'-(oxybis(ethane-2,1-diyl))dipyrrolidine

Step I: Preparation of 1,1'-(oxybis(ethane-2,1-diyl))bis(pyrrolidin-2-one)

A flask is filled with 100 g of 2,2'-oxybis(ethan-1-amine) and heated to 100° C. 165 g of γ-butyrolactone (GBL) is added dropwise and the solution is then stirred for 2 h. At the end of the addition, the mixture is stirred at 100° C. for a further 2 h. The mixture is then heated to 220° C. for 10 h and thereafter heated to 240° C. for a further 14 h with simultaneous removal of water by distillation. After cooling, the mixture was analyzed by gas chromatography. The mixture comprises 94.1% (area-%) of 1,1'-(oxybis(ethane-2,1-diyl))bis(pyrrolidin-2-one).

Step II: Preparation of a Mixture of 1,1'-(oxybis(ethane-2,1-diyl))dipyrrolidine and 1-(2-(2-(pyrrolidin-1-yl)ethoxy)ethyl)pyrrolidin-2-one 10 g of Grace Raney cobalt 2724 (50% slurry in $H_2O$) as catalyst is washed anhydrous with tetrahydrofuran (THF) and transferred to a 300 ml autoclave. The autoclave is filled with 50 g of 1,1'-(oxybis(ethane-2,1-diyl))bis(pyrrolidin-2-one) from step I and then closed. The autoclave is pressurized with 180 bar of $H_2$ and the mixture is heated to 170° C. for 48 h. After cooling and depressurizing, the resulting mixture is analyzed by gas chromatography. The mixture comprises 36.7% (area-%) of 1,1'-(oxybis(ethane-2,1-diyl)) dipyrrolidine and 47.2% (area-%) of 1-(2-(2-(pyrrolidin-1-yl)ethoxy)ethyl)pyrrolidin-2-one.

Step III: Preparation of 1,1'-(oxybis(ethane-2,1-diyl))dipyrrolidine 5 g of Grace Raney cobalt 2724 (50% slurry in $H_2O$) as catalyst is washed anhydrous with THF and transferred to a 300 ml autoclave. The autoclave is filled with 50 g of 1-(2-(2-(pyrrolidin-1-yl)ethoxy)ethyl)pyrrolidin-2-one from step II and then closed. The autoclave is pressurized with 180 bar of $H_2$ and the mixture is heated to 170° C. for 48 h. After cooling and venting, the resulting mixture is analyzed by gas chromatography. The mixture comprises 81.7% (area-%) of 1,1'-(oxybis(ethane-2,1-diyl))dipyrrolidine.

General Procedures for the Results of Tables 3-5 for the Hydrogenation

Hydrogenation of the Bisamide (1,1'-(oxybis(ethane-2,1-diyl))bis(pyrrolidin-2-one) with Raney-Co (Ra—Co)

Bisamide (100 g), Ra—Co (5 g), and optionally the percent amount of solvent and/or additive shown in tables 3-5, in which the percent value indicates the proportion of solvent and/or additive in the total amount, are transferred to an autoclave (internal volume 300 mL). The filled reactor is carefully filled with hydrogen to the pressure indicated in tables 3-5. The reaction is stirred at 500 rpm at the temperature indicated in tables 3-5. On reaching the reaction temperature indicated in tables 3-5, stirring under the reaction conditions is continued for the period of time indicated in tables 3-5. At the end of the time interval indicated in tables 3-5, the reactor is cooled to room temperature, depressurized, and opened. A dark solution containing the solid catalyst is obtained. For analysis purposes, a sample is investigated by gas chromatography.

Hydrogenation of the Bisamide (1,1'-(oxybis(ethane-2,1-diyl))bis(pyrrolidin-2-one) with the Catalysts in Tables 3 and 4 that are not Raney Co Bisamide (50 g), catalyst (5 g), and the percent amount of solvent shown in tables 3-5, in which the percent value indicates the proportion of solvent in the total mixture, are transferred to an autoclave (internal volume 300 mL). The filled reactor is carefully filled with hydrogen to the pressure indicated in tables 3-5. The reaction is heated to the reaction temperature indicated in tables 3-5 and stirred at 500 rpm. On reaching the desired reaction temperature, stirring under the reaction conditions is continued for the period of time indicated in tables 3-5. At the end of this reaction time as indicated in tables 3-5, the reactor is cooled to room temperature, depressurized, and opened. A dark solution containing the solid catalyst is obtained. For analysis purposes, a sample is investigated by gas chromatography.

Continuous Hydrogenation of the Bisamide (1,1'-(oxybis(ethane-2,1-diyl))bis(pyrrolidin-2-one) with Ra—Co in Accordance with Table 5

A 70 mL tubular reactor is filled with hydrogenation catalyst and the catalyst is optionally activated in a stream of hydrogen with application of heat. After activation, the reactor is continuously fed, at the temperature and pressure indicated in table 5, with a mixture of hydrogen, 1,1'-(oxybis(ethane-2,1-diyl))bis(pyrrolidin-2-one), and optionally solvent as specified in table 5 and the reaction output is analyzed by gas chromatography.

Table 1 shows the composition of the copper chromite type catalysts used. Table 2 comprises the temperature, pressure, solvents, and additives used with the preferred hydrogenation catalyst systems of the method of the invention.

TABLE 1

| BASF designation | Metal 1 | % by weight | Metal 2 | % by weight | Dopant | % by weight |
|---|---|---|---|---|---|---|
| Cu 0202 P | CuO | 83 | $Cr_2O_3$ | 17 | — | — |
| Cu 0396 P (E-396) | CuO | 48 | $Cr_2O_3$ | 48 | $MnO_2$ | 4 |
| Cu 1800P | CuO | 52 | $Cr_2O_3$ | 48 | — | — |
| Cu 1885 P | CuO | 53 | $Cr_2O_3$ | 47 | — | — |
| Cu 1950 P | CuO | 47 | $Cr_2O_3$ | 46 | $MnO_2$ | 5.5 |
| E 108 P | CuO | 44 | $Cr_2O_3$ | 45 | BaO | 11 |

TABLE 2

| Catalyst system | Temperature range (° C.) | Pressure range (bar) | Solvent/Additive |
|---|---|---|---|
| Raney Co | 170-240 | 150-200 | Dibutylamine |
| Cu 0202 P | 170-270 | 100-300 | Hexane |
| E-396 | 170-270 | 100-300 | Hexane |
| Cu 1950 P | 170-270 | 100-300 | Hexane |
| E 108 P | 170-270 | 100-300 | Hexane |
| Cu 1885 P | 170-270 | 100-300 | Hexane |

Tables 3-5 show the different yields in the hydrogenation of 1,1'-(oxybis(ethane-2,1-diyl))bis(pyrrolidin-2-one) in the presence of different catalyst systems for different further parameters

TABLE 3

| Test | Pressure (bar) | Temperature (° C.) | Catalyst | Solvent/Additive | Reaction time (h) | Conversion (%) | Yield (% by GC) |
|---|---|---|---|---|---|---|---|
| 1 | 80 | 170 | Ra—Co | Monoglyme 90% | 12 | 100 | 51.3 |
| 2 | 260 | 170 | Ra—Co | — | 36 | 98.9 | 70.3 |
| 3 | 260 | 170 | Ra—Co | Monoglyme 90% | 24 | 100 | 71.5 |
| 4 | 180 | 170 | Ra—Co | — | 60 | 100 | 60.9 |
| 5 | 180 | 200 | Ra—Co | — | 15 | 87.6 | 26.5 |
| 6 | 180 | 200 | Ra—Co | Dibutylamine 10% | 15 | 95.3 | 28.0 |
| 7 | 180 | 200 | Cu—Cr/Ba E 108 P | — | 15 | 61.8 | 10.5 |
| 8 | 180 | 240 | Cu—Cr/Ba E 108 P | — | 15 | 77.2 | 19.3 |
| 9 | 180 | 240 | Cu—Cr/Ba E 108 P | Hexane 50% | 15 | 100 | 66.3 |
| 10 | 180 | 240 | Cu—Cr/Ba E 108 P | Hexane 25% | 12 | 100 | 59 |

TABLE 4

| Test | Pressure (bar) | Temperature (° C.) | Catalyst | Solvent/Additive | Reaction time (h) | Conversion (%) | Yield (% by GC) |
|---|---|---|---|---|---|---|---|
| 13 | 180 | 200 | Cu—Cr/Mn (Cu 1950 P) | — | 15 | 12.0 | 0.3 |
| 14 | 180 | 200 | Cu—Cr (Cu 1885 P) | — | 15 | 16.9 | 0.7 |

TABLE 5

| Test | Pressure (bar) | Temperature (° C.) | Catalyst | Solvent/Additive | Loading (kg/L*h) | Conversion (%) | Yield (% by GC) |
|---|---|---|---|---|---|---|---|
| 15 | 200 | 170 | Ra—Co | — | 0.21 | 87.8 | 25.4 |
| 16 | 200 | 190 | Ra—Co | — | 0.21 | 99.0 | 51.8 |
| 17 | 200 | 190 | Ra—Co | THF (25%) | 0.21 | 99.3 | 55.2 |
| 18 | 200 | 190 | Ra—Co | THF (50%) | 0.14 | 99.9 | 48.1 |

The invention claimed is:

1. A method for preparing bispyrrolidine compounds of the formula (I)

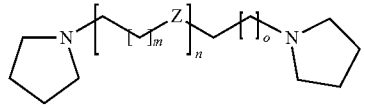

Formula I where

Z is oxygen, n is a whole natural number selected from 1, m and o are independently a natural number selected from 1 to 12, comprising reacting, in a step I) γ-butyrolactone with diamines of formula II

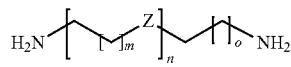

Formula II where Z, n, m, and o are as defined above, to form bisamides of the formula III and,

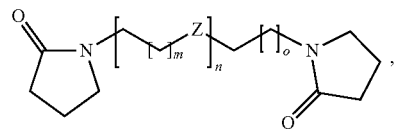

Formula III catalytically hydrogenating, in a step II), the bisamides of the formula III to form the bispyrrolidine compounds of formula I.

2. The method as claimed in claim 1, wherein step I) is carried out at temperatures in the range from 100 to 300° C. with simultaneous or subsequent removal of the excess water by distillation.

3. The method as claimed in claim 1, wherein step II) is carried out in the presence of a hydrogenation catalyst in which the hydrogenation catalyst comprises at least one metal selected from the group consisting of Cu, Cr, Ni, Co, Fe, Pt, Pd, Re, Ru, and Rh.

4. The method as claimed in claim 1, wherein step II) is carried out using a heterogeneous catalyst.

5. The method as claimed in claim 1, wherein step II) is carried out in the presence of a Raney cobalt, Raney nickel or doped or undoped catalyst of the Cu—Cr type.

6. The method as claimed in claim 1, wherein the hydrogenation in step II) is carried out in the presence of a Raney cobalt catalyst or of a doped catalyst of the Cu—Cr type at temperatures in the range from 100 to 300° C. and at a hydrogen pressure in the range from 100 to 350 bar.

7. The method as claimed in claim 1, wherein, in the bispyrrolidine compounds of the formula I, Z=oxygen, n=1, and m=o=1.

* * * * *